United States Patent [19]

Fleming et al.

[11] 3,957,988
[45] May 18, 1976

[54] ANTIVIRAL COMPOSITIONS CONTAINING BIS-BASIC KETONES OF THIOXANTHENE

[75] Inventors: Robert W. Fleming, Ann Arbor, Mich.; Arthur D. Sill, Greenhills, Ohio

[73] Assignee: Richardson-Merrell Inc., Wilton, Conn.

[22] Filed: Feb. 20, 1973

[21] Appl. No.: 334,075

Related U.S. Application Data

[63] Continuation-in-part of Ser. No. 137,055, April 23, 1971, Pat. No. 3,856,789.

[52] U.S. Cl.............................. 424/248; 424/244; 424/251; 424/267; 424/274; 424/275
[51] Int. Cl.$^2$............................................. A01N 9/00
[58] Field of Search .......... 424/250, 248, 267, 274, 424/275, 283

[56] References Cited
UNITED STATES PATENTS
3,767,674  10/1973  Nabih ................................ 260/328

OTHER PUBLICATIONS
Cecil et al., A Textbook of Medicine, 9th Ed., W. B. Saunders Co., Phila., Pa., 1958, p. 1.

*Primary Examiner*—Richard L. Huff
*Attorney, Agent, or Firm*—George W. Rauchfuss, Jr.; Eugene O. Retter

[57] ABSTRACT

The novel bis-basic ketones of thioxanthene have antiviral activity when administered orally and parenterally. These compounds are represented by the following formula:

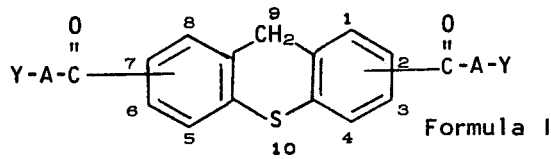

Formula I wherein A is a straight or branched alkylene chain having from 1 to about 6 carbon atoms; and each Y is A. the group

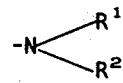

wherein $R^1$ and $R^2$ are individually hydrogen or lower alkyl having from 1 to about 4 carbon atoms; or B. the group

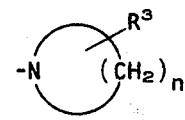

wherein n is a whole integer of 4 or 5, and $R^3$ is hydrogen or lower alkyl having from 1 to about 4 carbon atoms and can be linked to any one of the carbon atoms of the heterocyclic group; or C. the group

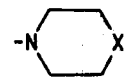

wherein X is oxygen or $NR^4$, and $R^4$ is hydrogen or lower alkyl of from 1 to about 4 carbon atoms; or pharmaceutically acceptable acid addition salts of said base.

These new compounds can be prepared by several different methods which are described.

32 Claims, No Drawings

ANTIVIRAL COMPOSITIONS CONTAINING BIS-BASIC KETONES OF THIOXANTHENE

RELATED APPLICATIONS

This application is a continuation-in-part of application Ser. No. 137,055 filed Apr. 23, 1971, now U.S. Pat. 3,856,789 issued Dec. 24, 1974.

FIELD OF INVENTION

This invention relates to novel bis-basic ketones of thioxanthene, their method of preparation and use as antiviral agents.

SUMMARY OF INVENTION

The compounds of this invention include both the base form and pharmaceutically acceptable acid addition salts thereof wherein the base form is represented by the formula:

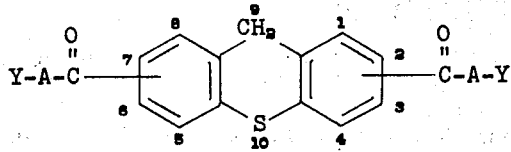

Formula I wherein A is a straight or branched alkylene chain having from 1 to about 6 carbon atoms; and each Y is
A. the group

wherein $R^1$ and $R^2$ are individually hydrogen or lower alkyl having from 1 to about 4 carbon atoms; or
B. the group

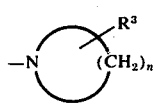

wherein $n$ is a whole integer of 4 or 5, and $R^3$ is hydrogen or lower alkyl having from 1 to about 4 carbon atoms and can be linked to any one of the carbon atoms of the heterocyclic group; or
C. the group

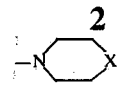

wherein X is oxygen or $NR^4$, and $R^4$ is hydrogen or lower alkyl of from 1 to about 4 carbon atoms; or pharmaceutically acceptable acid addition salts of said base.

DETAILED DESCRIPTION OF INVENTION

It can be seen from the above Formula I that the basic ketone groups, that is,

can be linked to the tricyclic ring system of thioxanthene by replacement of any of the four hydrogens of the benzenoid ring to which such group is attached. Thus, one of the groups can be in any of the positions 1 through 4 of the tricyclic ring system, and the other can be in any of the positions 5 through 8. Preferably one of the basic ketone groups is in the 2-position and the other is in the 7-position of the thioxanthene nucleus.

It is apparent from the above Formula I and its description that the compounds can have structures wherein Y is the group

as more fully shown by general Formula II, or wherein Y is the group

as more fully shown by general Formula III, or wherein Y is the group

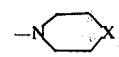

as more fully shown by general Formula IV below:

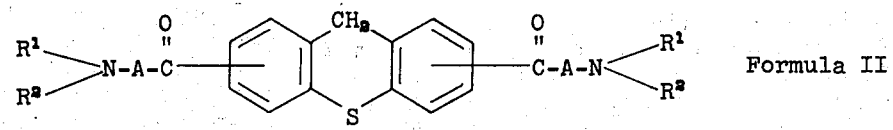

Formula II

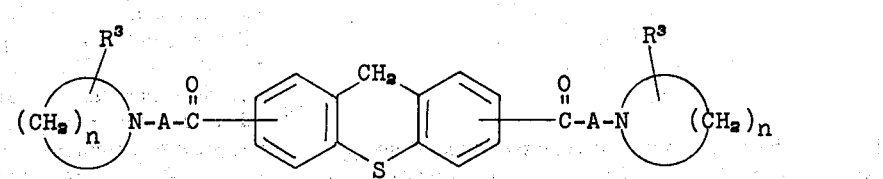

Formula III

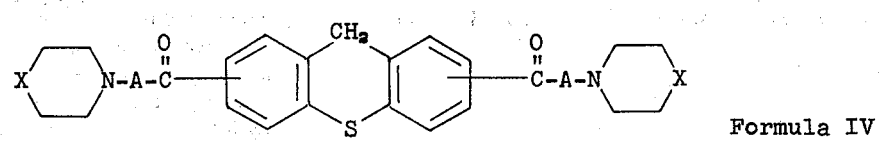

Formula IV

In the general Formulas II, III and IV the various symbols A, $R^1$, $R^2$, $R^3$, and X and $n$ have the meanings defined hereinbefore.

Each of the symbols A in the compounds of the above Formulas I, II, III and IV is an alkylene group having from 1 to about 6 carbon atoms which can be straight chain, that is, for example, $-CH_2-(CH_2)_m-$ wherein $m$ is a whole integer from 0 to 5, or a branched chain. Each of the alkylene groups as represented by A can be the same or different. Preferably these groups are the same. Illustrative of alkylene groups as represented by A there can be mentioned, for example: methylene, 1,2-ethylene, 1,3-propylene, 1,4-butylene, 1,5-pentylene, 1,6-hexylene, 2-methyl-1,4-butylene, 2-ethyl-1,4-butylene, 3-methyl-1,5-pentylene and the like.

Each amino group of the compounds of Formula II, that is,

can be a primary, a secondary or a tertiary amino group. Each $R^1$ and $R^2$ is individually hydrogen or lower alkyl having from 1 to about 4 carbon atoms. Preferably each of the amino groups as represented by

is a tertiary amino group.

The term lower alkyl as used in reference to the compounds of Formula II relates to straight or branched alkyl chains having from 1 to about 4 carbon atoms. Illustrative of lower alkyls as can be represented by each $R^1$ or $R^2$ in the compounds of Formula II there can be mentioned for example: methyl, ethyl, n-propyl, isopropyl, n-butyl and secondary-butyl.

Each heterocyclic group in the compounds of Formula III, that is,

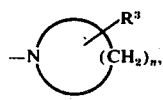

can be a 5- or 6-membered ring, that is, n is 4 or 5. The $R^3$ group can be hydrogen or a lower alkyl chain of from 1 to about 4 carbon atoms and can be attached to any one of the heterocyclic carbon atoms. Illustrative of heterocyclic groups as represented by each

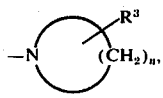

there can be mentioned, for example: piperidino, pyrrolidino, 4-methylpiperidino, 3-methylpiperidino, 4-propylpiperidino and the like.

Each heterocyclic group of Formula IV, that is,

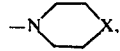

in addition to the one nitrogen atom, can contain a second hetero atom, that is, X is oxygen or $N-R^4$. The $R^4$ group can be hydrogen or a straight or branched lower alkyl chain of from 1 to about 4 carbon atoms. As examples of heterocyclic groups as represented by

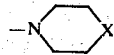

there can be mentioned, for example: morpholino, piperazino, N-(lower)alkylpiperazino, such as, for example, N-methyl- or N-ethylpiperazino and the like.

The preferred compounds of this invention are of the following general formula:

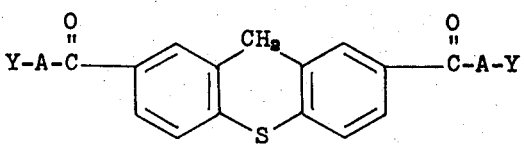

Formula V wherein each A is an alkylene chain of from 1 to 4 carbon atoms and each Y is selected from A. the group

wherein each $R^1$ and $R^2$ represents an alkyl chain of from 1 to 3 carbon atoms, B. the group

or

C. the group

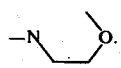

Illustrative of compounds of this invention there can be mentioned: 2,7-bis[2-(diethylamino)acetyl]thioxanthene, 2,7-bis[2-(dimethylamino)acetyl]thioxanthene, 2,7-bis[3-(dibutylamino)propionyl]thioxanthene, 2,7-bis[5-(dipropylamino)valeryl]thioxanthene, 2,7-bis(4-piperidinobutyryl)-thioxanthene, 2,7-bis[6-(1-piperazinyl)caproyl]thioxanthene, 2,7-bis[5-(dimethylamino)valeryl]thioxanthene, 2,5-bis[3-(diethylamino)propionyl]thioxanthene, 3,5-bis[4-(dimethylamino)butyryl]thioxanthene, 1,6-bis[2-(dibutylamino)acetyl]-thioxanthene, and the like.

Pharmaceutically acceptable acid addition salts of the base compounds of this invention are those of any suitable inorganic or organic acids. Suitable inorganic acids are, for example, hydrochloric, hydrobromic, sulfuric or phosphoric acids and the like. Suitable organic acids are, for example, carboxylic acids such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic, 2-phenoxybenzoic and the like, or sulfonic acids such as methane sulfonic, 2-hydroxyethane sulfonic acid and the like. Mono- or di-acid salts may be formed, and the salts can be hydrated or substantially anhydrous.

It has been found that the compounds of this invention are effective for inactivating or inhibiting a broad variety of viruses and can thus be employed as antiviral agents. These compounds are effective for preventing or inhibiting characteristic viral disease symptoms in a host by a wide variety of methods of application and composition. They can be administered for an antiviral effect by means which subject the host, or such host and a virus, to the active ingredients. The host is subjected to the active ingredients by bringing together an active ingredient and host, for example, by applying or contacting the host with such active ingredient or simply administering the active ingredient to the host. This includes subjecting the host to such active ingredient prior to infection with a virus, that is, prophylactic use, as well as subjecting the host to such active ingredient after infection, that is, therapeutic use. Thus, in viable biological material hosts subjected to the active ingredients, the replication of viruses is inhibited when the host is infected before or after being subjected to such ingredients. Also, administration by various routes of the active ingredients to an animal host prior to or after infection with the virus prevents or inhibits viral replication and the development of the various disease conditions characteristic of the particular virus. By the term "infection" we simply mean invasion of the host with a pathogenic virus. By the term "host" we mean viable biological material or intact animals which are capable of inducing the formation of interferon and which can support the replication of a virus. Preferably the host is of animal and particularly warm blooded or mammalian origin. Illustrative of hosts for various viruses there can be mentioned viable biological material such as can be used in the production of vaccines, for example, tissue cultures such as that of kidney, lung, amnion cells, embryos, for example, chick allantoic fluid; and various animals, for example, warm blooded animals such as birds or mammals, including mice, rats, guinea pigs, gerbils, ferrets and the like.

The mode of activity of the active ingredients is not rigorously defined. Inter alia, the active ingredients induce the formation of interferon when a host is subjected to such ingredients. Interferon is a known antiviral substance which is involved with the inhibition of the replication of viruses in the presence of a host cell. Some of the viruses susceptible to replication inhibition by interferon are set forth in Horsfall and Tamm, "Viral and Rickettsial Infections of Man", 4th Edition (1965), J.B. Lippencott Company, pages 328–329.

The compounds of the invention can be administered to animals such as warm blooded animals and particularly mammals to prevent or inhibit infections of picornavirus, for example, encephalomyocarditis; myxovirus, for example, Influenza $A_2$ (Jap/305); arbovirus, for example, Semliki forest; Herpes virus group, for example, herpes simplex; and poxviruses; for example, Vaccinia IHD. When administered prior to infection, that is, prophylactically, it is preferred that the administration be within 0 to 96 hours prior to infection of the animal with pathogenic virus. When administered therapeutically to inhibit an infection, it is preferred that the administration be within about a day or two after infection with pathogenic virus.

The dosage administered will be dependent upon the virus for which treatment or prophylaxis is desired, the type of animal involved, its age, health, weight, extent of infection, kind of concurrent treatment, if any, frequency of treatment and the nature of the effect desired. Illustratively, a daily dosage of the active ingredients will generally range from less than about 0.1 to over about 500 mg (milligram) per kg (kilogram) of body weight. Illustratively, dosage levels of the administered active ingredient can be intravenous, 0.1 to about 10 mg/kg; intraperitoneal, 0.1 to about 50 mg/kg; subcutaneous, 0.1 to about 250 mg/kg; oral, 0.1 to about 500 mg/kg and preferably about 1 to about 250 mg/kg; intranasal instillation, 0.1 to about 10 mg/kg; and aerosol, 0.1 to about 10 mg/kg of animal body weight.

The novel compounds, together with conventional pharmaceutical carriers can be employed in unit dosage forms such as solids, for example, tablets or capsules or liquid solutions, suspensions or elixirs for oral administration and injections, or liquid solutions, suspensions, emulsions and the like for parenteral use. The quantity of active ingredient in each dosage will generally differ depending on the type of unit dosage, the type of animal and its weight. Thus, each dosage can contain from less than about 2.0 mg to over 3 grams of active ingredients in a significant quantity of a non-toxic pharmaceutical carrier of the type that can be taken orally, applied topically, bucally or parenterally.

The pharmaceutical carrier can, as previously indicated, be a sterile liquid such as water and oils, with or without the addition of a surfactant. Illustrative of oils there can be mentioned those of petroleum, animal, vegetable or synthetic origin, for example, peanut oil, soybean oil, mineral oil, sesame oil, and the like. In general, water, saline, aqueous dextrose, and related sugar solutions and glycols such as propylene glycol or polyethylene glycol are preferred liquid carriers, particularly for injectable solutions. Sterile injectable solutions such as saline, for example, isotonic saline, will ordinarily contain from about 0.5% to 25% and preferably from about 1 to 10% by weight of the active ingredient in the composition.

As mentioned above, oral administration can be in a suitable suspension or syrup, in which the active ingredient ordinarily will constitute from about 0.5 to 10%, and preferably from about 1% to 5%, by weight. The pharmaceutical carrier in such composition can be a watery vehicle such as an aromatic water, a syrup or a pharmaceutical mucilage; also, a suspending agent for viscosity control such as magnesium aluminum silicate, carboxymethylcellulose or the like as well as a buffer, preservative, etc.

The active ingredients can also be admixed in animal feed or incorporated into the animal's drinking water. For most purposes, an amount of active ingredient will be used to provide from about 0.0001% to 0.1% by weight of the active ingredient based on the total weight of feed intake. Preferably, from 0.001% to 0.02% by weight will be used. The selection of the particular feed is within the knowledge of the art and will depend, of course, on the animal, the economics, natural materials available, and the nature of the effect desired.

The active ingredients can be admixed in animal feed concentrates, suitable for preparation and sale to farmers or livestock growers for addition to the animal's feedstuffs in appropriate proportion. These concentrates can ordinarily comprise about 0.5% to about 95% by weight of the active ingredient compounded together with a finely divided solid, preferably flours, such as wheat, corn, soya bean and cottonseed. Depending on the recipient animal, the solid adjuvant can be ground cereal, charcoal, fuller's earth, oyster shell and the like. Finely divided attapulgite and bentonite can also be used.

The feed compositions, as well as the feed concentrates, can additionally contain other components of feed concentrates or animal feeds, as will be readily understood. Other particularly important additives include proteins, carbohydrates, fats, vitamins, minerals, antibiotics, etc.

For use as aerosols the active ingredients can be packaged in a pressurized aerosol container together with a gaseous or liquefied propellant, for example, dichlorodifluoromethane, carbon dioxide, nitrogen, propane, etc. with the usual adjuvants such as co-solvents, and wetting agents, as may be necessary or desirable.

Typical surface active agents (Kirk and Othmer, *Encyclopedia of Chemical Terminology*, 1954, Vol. 13, page 513), particularly emulsifying and dispersing agents which can be used in the compositions of this invention are, for example, fatty alcohol sulfates such as sodium lauryl sulfate, aliphatic or aromatic sulfonates, such as sulfonated castor oil, and nonionic types of emulsifying or dispersing agents such as the high molecular weight alkyl polyglycol ethers, such as dodecyl polyglycol ethers containing from about 25 to 75 carbon atoms.

A desirable mode of administration for the compounds (active ingredients) of this invention is parenterally, such as by normally liquid injectable compositions, for example, for intramuscular or subcutaneous administration. In such compositions the quantity of active ingredient can vary from about 0.05% to 20% by weight of the composition and preferably from about 0.1% to 10% by weight. In order to minimize or eliminate irritation at the site of injection, the parenteral compositions can contain a non-ionic surfactant such as those having an HLB (hydrophile-lipophile balance) of about 12 to 17. Such formulations can be solutions, suspensions or emulsions in conventional liquid pharmaceutical carriers, for example, sterile liquids such as water, saline, and aqueous dextrose (glucose) and related sugar solutions. The quantity of surfactant in the formulation can vary from about 5% to 15% by weight of the formulation. The quantity of a compound of this invention, either in the base form or a pharmaceutically acceptable acid addition salt in such formulations, can vary over a broad range, such as that mentioned hereinbefore, that is, 0.05% to 20% by weight of the formulation. Preferably, the active ingredient is in the base form. The remaining component or components of such formulations can be a normally liquid pharmaceutical carrier, for example, isotonic aqueous saline, either alone or together with conventional excipients for injectable compositions. The surfactant can be a single surfactant having the above-indicated HLB or a mixture of two or more surfactants wherein such mixture has the indicated HLB. The following surfactants are illustrative of those which can be used in such formulations. (A) Polyoxyethylene derivatives of sorbitan fatty acid esters, such as the TWEEN series of surfactants, for example, TWEEN 80, and the like. The TWEENS are manufactured by Atlas Powder Company. (B) High molecular weight adducts of ethylene oxide with a hydrophobic base formed by the condensation of propylene oxide with propylene glycol, for example, PLURONIC F-68 which is manufactured by Wyandotte Chemical Company. The preferred surfactant is Polysorbate 80, U.S.P., a polyoxyethylene sorbitan monooleate.

One of the methods used to prepare the compounds of this invention is illustrated by the following:

Reaction 1

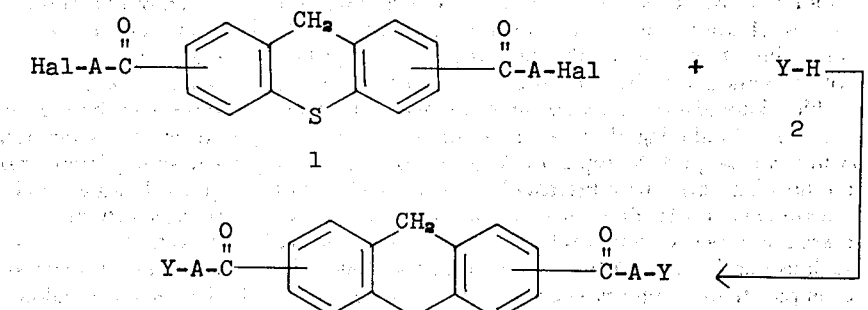

Formula I

In the above reaction scheme A and Y have the meanings defined hereinbefore and Hal is either chlorine, bromine or iodine.

The bis-(ω-haloalkanoyl)thioxanthene derivatives, 1, in which the position of substitution is 2,7-, can be prepared by a Friedel-Crafts acylation of thioxanthene. Of suitable acylating agents which may be used there can be mentioned, for example, chloroacetyl chloride, bromoacetyl bromide, 3-chloropropionyl chloride, 4-chlorobutyryl chloride, 5-chlorovaleryl chloride, 5-chloro-4-methylvaleryl chloride, 5-chloro-3-methylvaleryl chloride and the like.

It is apparent that the acylation reaction may be carried out in a variety of solvents and under catalysis of a variety of Lewis acids. The temperature and duration of the reaction may be varied to allow for optimum reaction conditions. A preferred procedure is to combine on equivalent of thioxanthene with 2.5 equivalents of an acylating agent in methylene chloride followed by portionwise addition of 2.2 equivalents of aluminum chloride. The temperature of the reaction is maintained below zero degrees with continuous stirring. After the additions are complete the temperature may be elevated to 25°–40°C. for 12 to 36 hours. The reaction mixture is worked up in the usual manner by decomposing the complex with ice water/HCl. The product obtained is recrystallized from methylene chloride, chloroform, or the like. The procedure may be varied such that there is a reverse addition of acylating agent and Lewis acid, or a reverse addition of aromatic hydrocarbon and Lewis acid. The more reactive halogen derivative, that is, the bis-(ω-iodoalkanoyl)thioxanthene may be prepared from the corresponding bis-chloro derivative using a halogen exchange reaction under the conditions generally employed in the Conant-Finkelstein reaction.

Of typical amines, 2, useful in the above reaction there can be mentioned, for example, ammonia, or a compound which is a potential source of ammonia such as, for example, hexamethylenetetramine and the like; primary amines such as ethylamine, propylamine and the like; and secondary amines such as diethylamine, dibutylamine, piperidine, 4-methylpiperidine, morpholine, piperazine, N-ethylpiperazine, and the like.

The amination of bis(ω-haloalkanoyl)thioxanthenes, 1, may be carried out under a variety of conditions. For example, compound 1 may be heated together with a large excess of the amine, 2, the excess amine serving as the reaction medium and the hydrohalide acceptor. This method is particularly suitable for readily available amines, the excess of which can be easily removed from the reaction mixture by, for example, distillation at reduced pressure or by washing the product with water. Or, one equivalent of compound 1 and four equivalents of the amine, 2, may be heated together in one of a number of different types of solvents, for example, in aromatic solvents such as benzene, toluene, xylene, and the like; or ethers such as tetrahydrofuran, dioxane and the like; or ketones such as acetone, butanone and the like; or aprotic solvents such as N,N-dimethylformamide, N,N-dimethylacetamide, dimethyl sulfoxide and the like; or mixtures of these solvents with water. The reaction between compound 1 wherein the halogen is chlorine and the amine, 2, is frequently promoted by the addition of either sodium or potassium iodide, the iodide being used in either catalytic or stoichiometric amounts. In some cases, it may be advantageous to use only two equivalents of the amine, 2, for each equivalent of the bis(ω-haloalkanoyl)thioxanthene, 1, an excess of an inorganic base such as powdered sodium or potassium carbonate being used as the hydrohalide acceptor. The reaction will proceed normally in 12 hours to two weeks at temperatures of −30° to 150°C. As volatile amines are employed, the reaction is best carried out under pressure in a suitable pressure reactor or autoclave.

Alternately, the amination reaction may be carried out on a derivative of compound 1 such as the thioxanthene ketal derivatives, which may be prepared by allowing bis-ω-haloalkanoylthioxanthene derivative and an excess of ethyl orthoformate to react in the presence of an acid catalyst such as hydrochloric acid for several days in a polar solvent such as ethanol, tetrahydrofuran and the like. The aminoketal derivative is hydrolyzed to the product of the invention by warming with dilute acid.

The compounds of Formula I wherein A is an alkylene chain of 3 to 6 carbon atoms may also be prepared by the reaction of a Grignard reagent with a bis-ester of bis-amide of thioxanthene as represented by the following:

Reaction 2

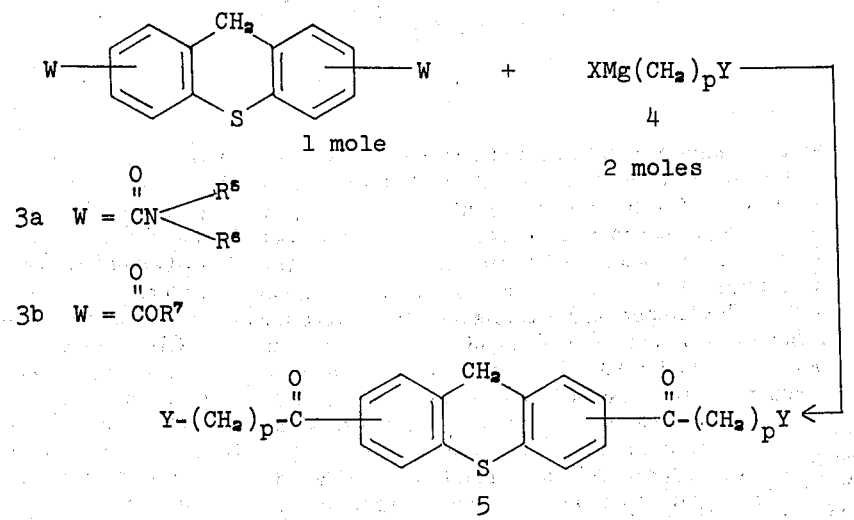

In the above reaction $R^5$ and $R^6$ are hydrogen or lower alkyl, or $-NR^5R^6$ taken together form a saturated monocyclic heterocyclic group such as piperidino or pyrrolidino; $R^7$ may be a straight or branched lower alkyl chain, or an aryl group such as phenyl, benzyl and the like; X is bromine or chlorine, p is an integer of from 3 to 6 and Y may be any of the groups defined hereinbefore except those which contain a hydrogen attached to the nitrogen.

The addition of the Grignard reagent, 4, is carried out at low temperatures ranging from −70° to 0°C., and the reaction mixture is then warmed at 0° to 80°C. for 1 to 24 hours.

The Grignard reagent, 4, may be prepared by reacting magnesium and an aminoalkyl halide of the formula $X(CH_2)_pY$ wherein X, p and Y have the meanings defined hereinabove.

The thioxanthene bis-amides and bis-esters, 3a and 3b, may be prepared by generally known methods from the corresponding thioxanthene bis-acids. These may be obtained among other procedures by reduction of the corresponding thioxanthen-9-one bis-acids by known methods such as the Wolff-Kishner reduction or by reduction with sodium and alcohol. The thioxanthen-9-one bis acids may be prepared by a procedure similar to that described by F. Gialdi, et al., in Farmaco Ed. Sci. 14, 830 (1959) for preparing thioxanthen-9-one mono acid.

The compounds of Formula I wherein A is $-CH_2CH_2-$ and Y is any of the groups defined hereinbefore, except those which contain two hydrogens on the nitrogen atom, may also be prepared by the Mannich reaction as represented by the following:

Reaction 3

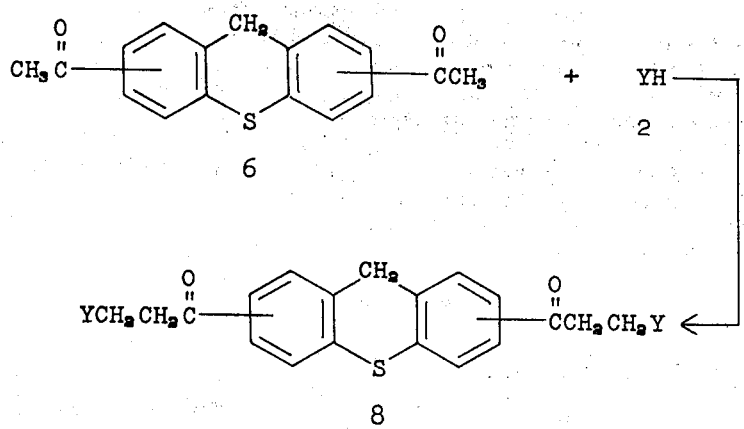

By combining one equivalent of compound 6 and two or more equivalents of compound 2 with three or more equivalents of formaldehyde, 7, the reaction will proceed in from a few minutes to 24 hours in solvents such as water, acetic acid, ethanol, butanol, dioxane, tetrahydrofuran and the like and at temperatures equivalent to the reflux temperature of the solvent. In this reaction either of two sources of formaldehyde may be employed. When formalin is used the reaction may be conducted with a suspension of compound 6 or a cosolvent such as methanol may be added to allow the reaction to proceed in a homogeneous medium. When the source of formaldehyde is paraformaldehyde the reaction is carried out in an organic solvent such as those mentioned above. It is sometimes desirable to add a slight excess of hydrochloric acid to promote depolymerization of paraformaldehyde either during the reaction or at the end of the reaction.

The secondary amine, compound 2, employed in this reaction may be added to the reaction medium as the hydrochloride salt or as the base form with subsequent in situ formation of the hydrochloride salt by the addition of hydrochloric acid. Of typical secondary amines which may be utilized in the above reaction there can be mentioned, for example, dimethylamine, dibutylamine, piperidine, 4-methylpiperidine, morpholine, N-ethylpiperazine and the like.

The diacetyl thioxanthene compound, 6, may be prepared by a Friedel-Crafts acylation reaction on thioxanthene or by a reaction of a thioxanthene bis-acid chloride with dimethylcadmium, which can be prepared from methyl Grignard and cadmium chloride. The thioxanthene bis-acid chloride may be prepared from the corresponding bis-acids by conventional procedures.

The intermediate, compound 1, wherein A is —$CH_2$—, may also be prepared by halogenation of the corresponding diacetyl compounds using conventional procedures such as cupric bromide.

Compounds of Formula I wherein Y is —$NH_2$, and A is a straight or branched alkylene chain having from 2 to 6 carbon atoms can be prepared by the following reaction:

Reaction 4

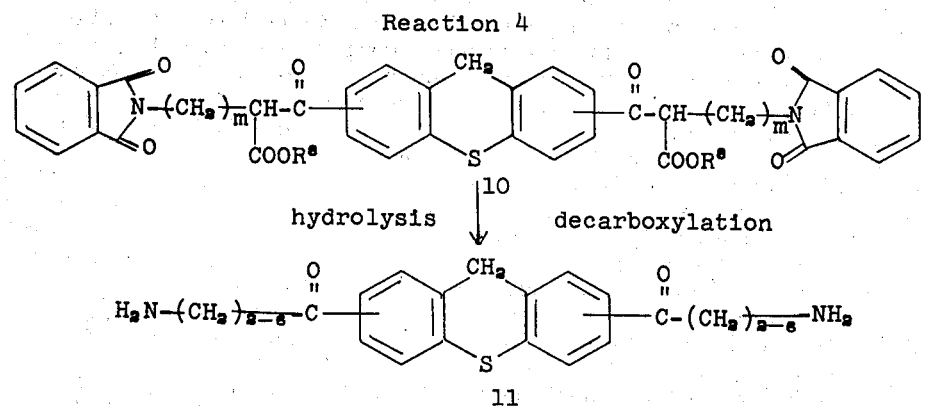

In the above reaction m is 1 to 5 and $R^8$ is a lower alkyl group. Hydrolysis and decarboxylation of the bis-phthalimido derivative, compound 10, can be carried out in solvents such as water, or lower alcohols such as ethanol, n-butanol and the like in the presence of acetic acid or mineral acids such as hydrochloric acid, sulfuric acid and the like, or mixtures of these acids. The reaction will proceed in from 5 minutes to 48 hours at temperatures equivalent to the reflux temperature of the solvent.

The bis-phthalimido derivative, compound 10, may be prepared by an ester condensation [J. Shivers et al., J. Am. Chem. Soc. 69, 119 (1947)] of a phthalimidoalkyl ester with a thioxanthene bis-lower alkyl ester, the preparation of which has been described hereinbefore.

EXAMPLES

Representative compounds of the present invention and several of the methods of preparing them, mentioned above, are illustrated in the following specific examples.

EXAMPLE 1

2,7-Bis[2-(diethylamino)acetyl]thioxanthene dihydrochloride hydrate

A mixture of 35.1 g (0.10 mole) of 2,7-bis(2-chloroacetyl)thioxanthene, 2 g of potassium iodide, 200 ml of diethylamine and 500 ml of tetrahydrofuran was warmed on a steam bath and allowed to stand at room temperature for 7 days with occasional shaking then filtered. The filtrate was evaporated to dryness leaving a residue which was dissolved in dilute HCl and filtered. The filtrate was made alkaline, extracted with methylene chloride, washed with water then saturated NaCl solution, dried over magnesium sulfate and filtered. The filtrate was acidified with ethereal HCl, and the resulting product was recrystallized from diethyl ether and methanol. After drying in vacuo and hydrating in a constant humidity chamber, the desired product was obtained. M.P. 122°–124°C.

EXAMPLE 2

2,7-Bis[3-(diethylamino)propionyl]thioxanthene dihydrochloride dihydrate

A mixture of 13.0 g (0.034 mole) of 2,7-bis(3-chloropropionyl)thioxanthene, 1 g of potassium iodide, 75 ml of diethylamine and 75 ml of tetrahydrofuran was allowed to stand for 72 hours and filtered. The residue was washed with tetrahydrofuran, evaporated to dryness then dissolved in ethanol. The solution was treated with ethanolic HCl, diluted with diethyl ether and the resulting solid was filtered off, recrystallized from methanol and diethyl ether and hydrated in a constant humidity chamber to give the desired product. M.P. 137°–140°C.

EXAMPLE 3

2,7-Bis[4-(diethylamino)butyryl]thioxanthene dihydrochloride

A mixture of 32.6 g (0.08 mole) of 2,7-bis(4-chlorobutyryl)thioxanthene, 2 g of potassium iodide, 100 ml of diethylamine and 100 ml of tetrahydrofuran was heated for 24 hours with stirring in a Paar bomb at 110°C. Upon cooling the mixture was evaporated to near dryness. The residue was dissolved in methylene chloride, washed with water then with saturated NaCl solution, dried over magnesium sulfate and filtered. The filtrate was evaporated to near dryness and recrystallized several times from methanol-diethyl ether and from acetone-methanol to give the desired product. M.P. 188°–191°C.

EXAMPLE 4

2,7-Bis(4-piperidinobutyryl)thioxanthene dihydrochloride monohydrate

A mixture of 40.7 g (0.10 mole) of 2,7-bis(4-chlorobutyryl)-thioxanthene, 1 g of potassium iodide and 200 ml of piperidine was stirred and heated on a steam bath for 72 hours. Upon cooling the solution was poured into 1 liter of water. The oily product obtained was dissolved in chloroform, washed with water then saturated NaCl solution, dried over magnesium sulfate and filtered. The filtrate was evaporated to a small volume, cooled, acidified to Congo Red with ethereal HCl and filtered. The resulting solid was recrystallized several times from ethanol to give the desired product. M.P. 229°–231°C.

EXAMPLE 5

2,7-Bis(4-morpholinobutyryl)thioxanthene

A mixture of 44.4 g (0.08 mole) of 2,7-bis(4-chloro-1,1-diethoxybutyryl)thioxanthene, 2 g of potassium iodide, 100 ml of morpholine and 100 ml of tetrahydrofuran was heated with stirring for 24 hours in a Paar bomb. Upon cooling the solution was filtered and the filtrate was evaporated to dryness. The residue was treated with 200 ml of 5% hydrogen chloride, refluxed for one hour and filtered. The filtrate was made alkaline with 20% NaOH solution, extracted with methylene chloride and filtered. The resulting solid was chromatographed on a column of silica gel using benzene-hexane as the eluant, recrystallized several times from benzene-heptane and acetone and dried in vacuo to give the desired product. M.P. 90.5°–91.5°C.

EXAMPLE 6

2,7-Bis[5-(dimethylamino)valeryl]thioxanthene dihydrochloride

A mixture of 20.0 g (0.046 mole) of 2,7-bis(5-chlorovaleryl)thioxanthene, 2 g of potassium iodide, 200 ml of 40% dimethylamine and 100 ml of tetrahydrofuran was heated in a Paar bomb to 105°C. for 24 hours. Upon cooling, the mixture was evaporated to near dryness. The residual oil was dissolved in methylene chloride, washed with water, dried over magnesium sulfate, filtered and acidified to Congo Red with ethereal HCl. The resulting precipitate was filtered off and recrystallized several times from methanol and ethyl acetate to give the desired product. M.P. 232°–234.5°C.

EXAMPLE 7

2,7-Bis(5-piperidinovaleryl)thioxanthene

A mixture of 20 g of 2,7-bis(5-chlorovaleryl)thioxanthene, 2 g of potassium iodide, 70 ml of piperidine and 150 ml of tetrahydrofuran was heated in a Paar bomb at 100°C. with stirring for 48 hours. Upon cooling, the solvent was evaporated, and the remaining material was poured into water then filtered. The residue was recrystallized several times from heptane to give the desired product. M.P. 98.5°–99.5°C.

EXAMPLE 8

2,7-Bis[5-(diethylamino)valeryl]thioxanthene dihydrochloride

A mixture of 20 g (0.0046 mole) of 2,7-bis(5-chlorovaleryl)-thioxanthene, 2 g of potassium iodide, 150 ml of diethylamine and 250 ml of tetrahyrofuran was heated to 106°C. in a Paar bomb for 24 hours with stirring. Upon cooling, the solvent was evaporated, and the remaining material was dissolved in heptane and filtered. The solution was acidified with ethereal HCl and the resulting precipitate was recrystallized several times from methanol and ethyl acetate to give the desired product. M.P. 197.5°–199.5°C.

EXAMPLE 9

Following the procedure of Example 7, only substituting for piperidine an appropriate amount of pyrrolidine, N-methylpiperazine, 4-methylpiperidine or 4-propylpiperidine, the following compounds are obtained:

2,7-bis(5-pyrrolidinovaleryl)thioxanthene,
2,7-bis[5-(4-methyl-1-piperazinyl)valeryl]thioxanthene,
2,7-bis[5-(4-methylpiperidino)valeryl]thioxanthene,
2,7-bis[5-(4-propylpiperidino)valeryl]thioxanthene.

EXAMPLE 10

Following the procedure of Example 3, only substituting for 2,7-bis(4-chlorobutyryl)thioxanthene an appropriate amount of 2,7-bis(4-chlorovaleryl)thioxanthene or 2,7-bis(4-chloro-2-methylbutyryl)thioxanthene, the following compounds are prepared:

2,7-bis(4-diethylaminovaleryl)thioxanthene,
2,7-bis(4-diethylamino-2-methylbutyryl)thioxanthene.

EXAMPLE 11

2,5-Bis[4-(diethylamino)butyryl]thioxanthene

A. 10-thioxanthene-9-one-2,5-dicarboxylic acid, which is prepared from o-mercaptobenzoic acid and 4-bromoisophthalic acid by the method described by F. Gialdi et al., Farmaco Ed. Sci. 14, 830 (1959), is reduced to thioxanthene 2,5-dicarboxylic acid by a Wolff-Kishner reduction [N. Ishikawa, Yuki Gosei Kagaku Kyokai 17, 553–6 (1959); CA 54:450]. The thioxanthene dicarboxylic acid derivative is converted to thioxanthene-2,5-dipiperidide by conventional procedures.

B. To a cooled solution of thioxanthene-2,5-dipiperidide in anhydrous tetrahydrofuran is added a solution of 3-(diethylamino)propyl magnesium chloride, prepared from magnesium and 3-(diethylamino)propyl chloride in tetrahyrofuran. The reaction mixture is warmed slowly to room temperature and stirred for 24 hours. The Grignard complex is decomposed by treating the reaction mixture with a solution of ammonium chloride, and the product is isolated and purified by conventional procedures.

EXAMPLE 12

3,5-Bis[4-(dimethylamino)butyryl]thioxanthene

A. Following the procedure of Example 11A, only substituting for 4-bromoisophthalic acid an appropriate amount of 2-bromoterephthalic acid, thioxanthene-3,5-dipiperidide is obtained.

B. To a cooled solution of thioxanthene-3,5-dipiperidide in anhydrous tetrahydrofuran is added a solution of 3-(dimethylamino)propyl magnesium chloride, prepared from magnesium and 3-(dimethylamino)propyl chloride in tetrahyrofuran. The reaction mixture is warmed slowly to room temperature and stirred for 24 hours after which the Grignard complex is decomposed by treating the reaction mixture with a solution of ammonium chloride, and the product is isolated and purified by conventional procedures.

EXAMPLE 13

1,6-Bis[4-(dimethylamino)butyryl]thioxanthene

Following the procedure of Example 11A, only substituting for 4-bromoisophthalic acid and o-mercaptobenzoic acid appropriate amounts of 3-bromophthalic acid and m-mercaptobenzoic acid respectively, thioxanthene-1,6-dicarboxylic acid is obtained and subsequently converted to the dipiperidide by conventional procedures.

By the procedure of Example 12B, only substituting for thioxanthene-3,5-dipiperidide an appropriate amount of thioxanthene-1,6-dipiperidide, the desired product is obtained.

EXAMPLE 14

4,5-Bis[3-(diethylamino)propionyl]thioxanthene Dihydrochloride

By the procedure of Example 11A, only substituting for 4-bromoisophthalic acid an appropriate amount of 2-bromoisophthalic acid, thioxanthene-4,5-dicarboxylic acid is obtained and converted to the bis-acid chloride by conventional procedures. By a reaction of the bis-acid chloride with dimethyl cadmium, prepared from methyl Grignard and cadmium chloride, 4,5-diacetylthioxanthene is obtained.

A mixture of 13.4 g (0.0477 mole) of 4,5-diacetylthioxanthene, 10.8 g (0.0985 mole) of diethylamine hydrochloride, 4.7 g (0.156 mole) of para-formaldehyde and 50 ml of isoamyl alcohol is stirred and refluxed for 15 minutes. The reaction mixture is cooled, treated with anhydrous ether, and the resulting solid filtered and recrystallized from chloroform-ethyl acetate to give the desired product.

EXAMPLE 15

2,7-Bis(4-aminobutyryl)thioxanthene Dihydrochloride 2,7-Bis(4-phthalimidobutyryl)thioxanthene, prepared from 4-phthalimidobutyryl chloride and thioxanthene by the method of S.S. Cheng et al., J. Med. Chem. 9, 945 (1966), is treated with hot glacial acetic acid after which concentrated HCl is added gradually with stirring. The mixture is heated to reflux for 24 hours with a constant stream of HCl gas passing through the mixture. The reaction mixture is stirred and refluxed for an additional 24 hours, cooled, and the product worked up in the usual manner.

EXAMPLE 16

2,7-Bis(2-chloroacetyl)thioxanthene

To a mixture of 99.18 g (0.5 mole) of thioxanthene, 141.0 g (1.25 mole) of 2-chloroacetyl chloride and 3 liters of dried methylene chloride, cooled to +20°C, was added slowly over ½ hour 146.7 g (1.1 mole) of aluminum chloride maintaining a temperature below +10°C. The reaction mixture was allowed to warm slowly to room temperature then refluxed for 4 hours. Upon cooling to room temperature, the mixture was decomposed by pouring into 2 liters of ice water and the layers were separated. The aqueous layer was extracted with methylene chloride after which the methylene chloride layers were combined and evaporated to a small volume and cooled. The resulting solid was filtered off and recrystallized from acetone to give the desired product. M.P. 175°–177°C.

EXAMPLE 17

2,7-Bis(3-chloropropionyl)thioxanthene

Following the procedure of Example 16, only substituting for 2-chloroacetyl chloride, 158.5 g (1.25 moles) of 3-chloropropionyl chloride, the desired product was obtained upon recrystallization from benzene-petroleum-ether and from benzene and heptane. M.P. 105°–107°C.

EXAMPLE 18

2,7-Bis(5-chlorovaleryl)thioxanthene

Following the procedure of Example 16, only substituting for 2-chloroacetyl chloride, 194 g (1.25 moles) of 5-chlorovaleryl chloride, the desired product was obtained upon recrystallization from benzene-petroleum-ether. M.P. 85°–86.5°C.

EXAMPLE 19

Following the procedure of Example 16, only substituting for 2-chloroacetyl chloride an appropriate amount of 4-chlorovaleryl chloride or 4-chloro-2-methylbutyryl chloride which can be prepared by treating respectively γ-valerolactone and α-methyl-γ-butryrolactone with thionyl chloride and anhydrous zinc chloride [O. Wheeler and E. de Rodriguez, J. Org. Chem. 29, 1227 (1964)] the following compounds are prepared: 2,7-bis(4-chlorovaleryl)thioxanthene, 2,7-bis(4-chloro-2-methylbutyryl)thioxanthene.

EXAMPLE 20

2,7-Bis(4-chlorobutyryl)thioxanthene

Following the procedure of Example 16, only substituting for 2-chloroacetyl chloride 173.3 g (1.25 moles) of 4-chlorobutyryl chloride the solid obtained was recrystallized from pentane and from heptane-benzene to give the desired product. M.P. 115°–116°C.

EXAMPLE 21

2,7-Bis(4-chloro-1,1-diethoxybutyl)thioxanthene

A mixture of 32.6 g (0.08 mole) of 2,7-bis(4-chlorobutyryl)-thioxanthene, 32.6 g (0.22 mole) of triethylorthoformate, 200 ml of dried absolute ethanol, 100 ml of tetrahydrofuran, and 5 ml of ethereal HCl was stirred for 24 hours in a stoppered flask. The solution was made alkaline with sodium methoxide in methanol and filtered. The filtrate was evaporated to dryness and cooled yielding the desired product.

EXAMPLE 22

2,7-Bis[5-(diallylamino)valeryl]thioxanthene

A mixture of 22.3 g (0.05 mole) of 2,7-bis(5-chlorovaleryl)thioxanthene, 1 g of potassium iodide, 100 ml of diallylamine and 200 ml of tetrahydrofuran was placed in a Paar bomb and heated to 120°C. with stirring for 24 hours. Upon cooling, the mixture was filtered and the filtrate evaporated to dryness. The resulting residue was dissolved in dilute HCl and extracted with ether. The aqueous portion was made basic, extracted with methylene chloride, dried over magnesium sulfate and filtered. The filtrate was heated to boiling, treated with charcoal, filtered and filtrate evaporated to dryness. The residue was chromatographed on a column of alumina and eluted with methylene chloride. The resulting oil was dissolved in diethyl ether, dried over molecular sieves, filtered and the ether evaporated. This process was repeated several times to yield the desired product.

EXAMPLE 23

An illustrative composition for a parenteral injection is the following wherein the quantities are on a weight to volume basis.

| | | |
|---|---|---|
| (a) | 2,7-bis[4-(diethylamino)butyryl]thioxanthene dihydrochloride | 100 mg. |
| (b) | Sodium chloride | q.s. |
| (c) | Water for injection to make | 10 ml. |

The composition is prepared by dissolving the active ingredient and sufficient sodium chloride in water for injection to render the solution isotonic. The composition may be dispensed in a single ampule containing 100 mg. of the active ingredient for multiple dosage or in 10 ampules for a single dosage.

EXAMPLE 24

An illustrative composition for hard gelatin capsules is as follows:

| | | Per Capsule |
|---|---|---|
| (a) | 2,7-bis[4-(diethylamino)butyryl]thioxanthene dihydrochloride | 200 mg. |
| (b) | Talc | 35 mg. |

The formulation is prepared by passing the dry powders of (a) and (b) through a fine mesh screen and mixing them well. The powder is then filled into No. 0 hard gelatin capsules at a net fill of 235 mg. per capsule.

EXAMPLE 25

An illustrative composition for tablets is as follows:

| | | Per Tablet |
|---|---|---|
| (a) | 2,7-bis[4-(diethylamino)butyryl]thioxanthene dihydrochloride | 100 mg. |
| (b) | Wheat starch | 15 mg. |
| (c) | Lactose | 33.5 mg. |
| (d) | Magnesium stearate | 1.5 mg. |

Preparation: A granulation obtained upon mixing lactose with the starch and granulated starch paste is dried, screened and mixed with the active ingredient and magnesium stearate. The mixture is compressed in tablets weighing 150 mg. each.

EXAMPLE 26

An illustrative composition for pills is as follows:

| | | Per Pill |
|---|---|---|
| (a) | 2,7-bis[4-(diethylamino)butyryl]thioxanthene dihydrochloride | 100 mg. |
| (b) | Starch, corn | 90 mg. |
| (c) | Liquid glucose | 10 mg. |

The pills are prepared by blending the active ingredient and starch and then adding the liquid glucose with thorough kneading to form a plastic mass. The pills are then cut and formed from the plastic pill mass.

EXAMPLE 27

A 2% weight per volume syrup of 2,7-bis[4-(diethylamino)butyryl]thioxanthene dihydrochloride can some of the headings are explained as follows: The "Challenge", that is, inoculation wih a virus used is generally fatal at all the untreated, that is, control, animals in the experiment. "Time of death" refers to the average time of death for the untreated animals. The "Treatment" was prophylactic or therapeutic or both. The term "volume" refers to the volume of composition administered per dose which contained the active ingredient dissolved in sterile water which also contained 0.15 percent of hydroxyethylcellulose. The control animals received a sham dosage of the same volume of the vehicle which did not contain the active ingredient. The abbreviation "STR" is survival time ratio, which is calculated by dividing the mean day of death of the control animals into the mean day of death of the treated animals during the period of observation. The activity of the compound in the example involved is further characterized, for example, low, medium, high, and the like. A survival time ratio (STR) of less than 0.90 indicates that the compound was toxic; a ratio of 0.90 to 1.09 indicates that there is no activity; a ratio of 1.10 to 1.19 indicates low or weak activity; a ratio of 1.20 to 1.29 indicates medium activity; and a ratio of 1.30 and greater indicates high activity.

Table I

| Example No. | Active Ingredient |
|---|---|
| 31 | 2,7-bis(4-piperidinobutyryl)thioxanthene dihydrochloride monohydrate. |
| 32 | 2,7-bis[5-(diethylamino)valeryl]thioxanthene dihydrochloride. |
| 33 & 34 | 2,7-bis(5-piperidinovaleryl)thioxanthene. |
| 35 | 2,7-bis[5-(dimethylamino)valeryl]thioxanthene dihydrochloride. |
| 36 | 2,7-bis[4-(diethylamino)butyryl]thioxanthene dihydrochloride. |
| 37 | 2,7-bis[2-(diethylamino)acetyl]thioxanthene dihydrochloride hydrate. |
| 38 | 2,7-bis(4-morpholinobutyryl)thioxanthene. | be prepared by the usual pharmaceutical techniques according to the following formula:

|  | Grams |
|---|---|
| (a) Finely divided 2,7-bis[4-(diethylamino)-butyryl]thioxanthene dihydrochloride | 2.0 |
| (b) Sucrose | 33.3 |
| (c) Chloroform | 0.25 |
| (d) Sodium benzoate | 0.4 |
| (e) Methyl p-hydroxybenzoate | 0.02 |
| (f) Vanillin | 0.04 |
| (g) Glycerol | 1.5 |
| (h) Purified water to 100.0 ml. |  |

EXAMPLE 28

2,7-Bis[4-(diethylamino)butyryl]thioxanthene dihydrochloride is mixed with soybean meal to prepare an animal feed concentrate containing 10 grams of said thioxanthene compound per pound of the medicated feed. This can subsequently be diluted with a mixed grain ration to give a medicated feed containing 50 milligrams of the thioxanthene per pound of the medicated feed.

EXAMPLE 29

The following formulation is illustrative of a dusting powder:

|  | Per Kilogram |
|---|---|
| (a) 2,7-bis[4-(diethylamino)butyryl]thioxanthene dihydrochloride | 20 grams |
| (b) Silica aerogel | 980 grams |

The dusting powder is prepared by intimately admixing the ingredients. The mixture is then packaged in dispensing containers.

EXAMPLE 30

An illustrative composition for a parenteral injection is the following aqueous emulsion.

| Each ml. contains | Ingredient | Amount |
|---|---|---|
| 50 mg. | 2,7-bis[4-(diethylamino)butyryl]-thioxanthene dihydrochloride | 1.000 g. |
| 100 mg. | Polyoxyethylene sorbitan monooleate | 2.000 g. |
| 0.0064 gm. | Sodium chloride | 0.128 g. |
|  | Water for injection, q.s. | 20.000 ml. |

The composition of Example 30 is prepared by dissolving 0.64 g. of sodium chloride in 100 ml. of water for injection; mixing the polyoxyethylene sorbitan monooleate with the thioxanthene, adding a sufficient solution of the sodium chloride in water to the active ingredient and polyoxyethylene sorbitan monooleate to make 20 ml; shaking the mixture; and then autoclaving it for 20 minutes at 110°C. at 15 p.s.i.g. steam pressure. The composition can be dispensed in a single ampule for multiple dosage or in 10 or 20 ampules for single dosages.

EXAMPLES 31 to 38

Examples 31 to 38 illustrate in vivo or in vitro antiviral studies with active ingredients of this invention. Each example recites pertinent information involved. Table I lists the active ingredient which was administered in each of the examples. Although it is believed that the headings in the examples of self-explanatory,

| Example No. | 31 | 32 | 33 |
|---|---|---|---|
| VIRUS | Encephalomyocarditis | Encephalomyocarditis | Encephalomyocarditis |
| type | RNA: Picornavirus | RNA; Picornavirus | RNA: Picornavirus |
| challenge | 27 $LD_{50}$ | 7 $LD_{50}$ | 10 $LD_{50}$ |
| route | Subcutaneous | Subcutaneous | Subcutaneous |
| time of death | 4.7 days | 4.3 days | 4.6 days |
| period of observation | 9 days | 9 days | 9 days |
| ANIMAL | Mice | Mice | Mice |
| weight | 12–15 grams | 12–15 grams | 12–15 grams |
| No. in treated group | 10 | 10 | 10 |
| No. in control group | 20 | 20 | 10 |
| TREATMENT | Prophylactic | Prophylactic and Therapeutic | Prophylactic and Therapeutic |
| dosage level | 50 mg/kg | 10 mg/kg | 10 mg/kg |
| route | Subcutaneous | Subcutaneous | Subcutaneous |
| volume | 0.25 ml. | 0.25 ml. | 0.25 ml. |
| time pre-challenge | 28, 22, 2 hrs. | 28, 22, 2 hrs. | 28, 22, 2 hrs. |
| post-challenge | None | 2 hrs. | 2 hrs. |

| Example No. | 31 | 32 | 33 |
|---|---|---|---|
| RESULTS | | | |
| STR | 2.13 | 1.58 | 1.76 |
| activity | High | High | High |

| Example No. | 34 | 35 | 36 |
|---|---|---|---|
| VIRUS | | | |
| type | Encephalomyocarditis RNA: Picornavirus | Encephalomyocarditis RNA: Picornavirus | Encephalomyocarditis RNA: Picornavirus |
| challenge | 10 $LD_{50}$ | 15 $LD_{50}$ | 18 $LD_{50}$ |
| route | Subcutaneous | Subcutaneous | Subcutaneous |
| time of death | 4.6 days | 4.3 days | 4.4 days |
| period of observation | 9 days | 9 days | 9 days |
| ANIMAL | | | |
| weight | Mice 12–15 grams | Mice 12–15 grams | Mice 12–15 grams |
| No. in treated group | 10 | 10 | 10 |
| No. in control group | 10 | 20 | 30 |
| TREATMENT | Prophylactic and Therapeutic | Prophylactic and Therapeutic | Prophylactic and Therapeutic |
| dosage level | 50 mg/kg | 10 mg/kg | 10 mg/kg |
| route | Oral | Subcutaneous | Subcutaneous |
| volume | 0.25 ml. | 0.25 ml. | 0.25 ml |
| time pre-challenge | 28, 22, 2 hrs. | 28, 22, 2 hrs. | 28, 22, 2 hrs. |
| post-challenge | 2 hrs. | 2 hrs. | 2 hrs. |
| RESULTS | | | |
| STR | 1.15 | 1.70 | 1.59 |
| activity | Weak | High | High |

| Example No. | 37 | 38 |
|---|---|---|
| VIRUS | | |
| type | Encephalomyocarditis RNA: Picornavirus | Encephalomyocarditis RNA: Picornavirus |
| challenge | 6 $LD_{50}$ | 26 $LD_{50}$ |
| route | Subcutaneous | Subcutaneous |
| time of death | 4.4 days | 4.2 days |
| period of observation | 9 days | 9 days |
| ANIMAL | | |
| weight | Mice 12–15 grams | Mice 12–15 grams |
| No. in treated group | 10 | 10 |
| No. in control group | 20 | 20 |
| TREATMENT | Prophylactic | Prophylactic and Therapeutic |
| dosage level | 250 mg/kg | 250 mg/kg |
| route | Subcutaneous | Subcutaneous |
| volume | 0.25 ml. | 0.25 ml. |
| time pre-challenge | 28, 22, 2 hrs. | 28, 22, 2 hrs. |
| post-challenge | None | 2 hrs. |
| RESULTS | | |
| STR | 1.34 | 2.12 |
| activity | High | High |

We claim:

1. A pharmaceutical composition for inhibiting viral infections, in unit dosage form, comprising a significant quantity of a pharmaceutically acceptable carrier and from about 0.1 milligram of 3 grams of a compound selected from a base of the formula

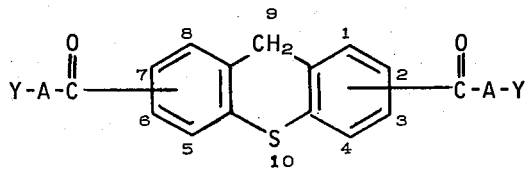

wherein A is a straight or branched alkylene chain having from 1 to about 6 carbon atoms; and each Y is
A. the group

wherein $R^1$ and $R^2$ are individually hydrogen, allyl or lower alkyl having from 1 to about 4 carbon atoms; or
B. the group

wherein $n$ is a whole integer of 4 or 5, and $R^3$ is hydrogen or lower alkyl having from 1 to about 4 carbon atoms and can be linked to any one of the carbon atoms of the heterocyclic group; or
C. the group

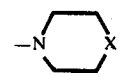

wherein X is oxygen or $NR^4$, and $R^4$ is hydrogen or lower alkyl of from 1 to about 4 carbon atoms; or a pharmaceutically acceptable acid addition salt thereof.

2. The composition of claim 1 wherein the compound has one of the

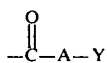

groups in the 2-position of the thioxanthene ring and the other such group is in the 7-position.

3. The composition of claim 2 wherein each Y of the compound is the group

4. The composition of claim 2 wherein each Y of the compound is the group

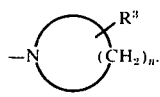

5. The composition of claim 4 wherein $n$ of the compound is the integer 5.

6. The composition of claim 2 wherein each Y of the compound is the group

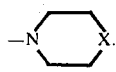

7. The composition of claim 6 wherein X of the compound is oxygen.

8. The composition of claim 2 wherein the compound is 2,7-bis[2-(diethylamino)acetyl]thioxanthene or a pharmaceutically acceptable acid addition salt thereof.

9. The composition of claim 2 wherein the compound is 2,7-bis[3-(diethylamino)propionyl]thioxanthene or a pharmaceutically acceptable acid addition salt thereof.

10. The composition of claim 2 wherein the compound is 2,7-bis[4-(diethylamino)butyryl]thioxanthene or a pharmaceutically acceptable acid addition salt thereof.

11. The composition of claim 2 wherein the compound is 2,7-bis(4-piperidinobutyryl)thioxanthene or a pharmaceutically acceptable acid addition salt thereof.

12. The composition of claim 2 wherein the compound is 2,7-bis(4-morpholinobutyryl)thioxanthene or a pharmaceutically acceptable acid addition salt thereof.

13. The composition of claim 2 wherein the compound is 2,7-bis[5-(dimethylamino)valeryl]thioxanthene or a pharmaceutically acceptable acid addition salt thereof.

14. The composition of claim 2 wherein the compound is 2,7-bis(5-piperidinovaleryl)thioxanthene or a pharmaceutically acceptable acid addition salt thereof.

15. The composition of claim 2 wherein the compound is 2,7-bis[5-(diethylamino)valeryl]thioxanthene or a pharmaceutically acceptable acid addition salt thereof.

16. The composition of claim 2 wherein the compound is 2,7-bis[5-(diallylamino)valeryl]thioxanthene or a pharmaceutically acceptable acid addition salt thereof.

17. A method of preventing or inhibiting viral infections susceptible to replication inhibition by interferon induction which comprises administering to a warm-blooded host having cells susceptible to invasion by pathogenic viral agents, within an antivirally effective time period, an antivirally effective amount of a compound selected from a base of the formula

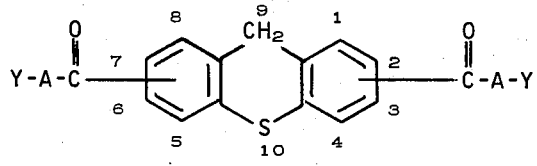

wherein A is a straight or branched alkylene chain having from 1 to about 6 carbon atoms; and each Y is A. the group

wherein $R^1$ and $R^2$ are individually hydrogen, allyl or lower alkyl having from 1 to about 4 carbon atoms; or B. the group

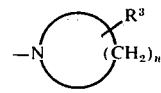

wherein $n$ is a whole integer of 4 or 5, and $R^3$ is hydrogen or lower alkyl having from 1 to about 4 carbon atoms and can be linked to any one of the carbon atoms of the heterocyclic group; or C. the group

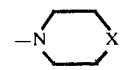

wherein X is oxygen or $NR^4$, and $R^4$ is hydrogen or lower alkyl of from 1 to about 4 carbon atoms; or a pharmaceutically acceptable acid addition salt thereof.

18. The method of claim 17 wherein the compound has one of the

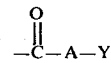

groups in the 2-position of the thioxanthene ring and the other such group is in the 7-position.

19. The method of claim 18 wherein each Y of the compound is the group

20. The method of claim 18 wherein each Y of the compound is the group

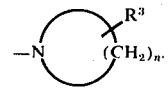

21. The method of claim 20 wherein *n* of the compound is the integer 5.

22. The method of claim 18 wherein each Y of the compound is the group

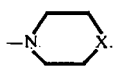

23. The method of claim 22 wherein X of the compound is oxygen.

24. The method of claim 18 wherein the compound is 2,7-bis[2-(diethylamino)acetyl]thioxanthene or a pharmaceutically acceptable acid addition salt thereof.

25. The method of claim 18 wherein the compound is 2,7-bis[3-(diethylamino)propionyl]thioxanthene or a pharmaceutically acceptable acid addition salt thereof.

26. The method of claim 18 wherein the compound is 2,7-bis[4-(diethylamino)butyryl]thioxanthene or a pharmaceutically acceptable acid addition salt thereof.

27. The method of claim 28 wherein the compound is 2,7-bis(4-piperidinobutyryl)thioxanthene or a pharmaceutically acceptable acid addition salt thereof.

28. The method of claim 18 wherein the compound is 2,7-bis(4-morpholinobutyryl)thioxanthene or a pharmaceutically acceptable acid addition salt thereof.

29. The method of claim 18 wherein the compound is 2,7-bis[5-(dimethylamino)valeryl]thioxanthene or a pharmaceutically acceptable acid addition salt thereof.

30. The method of claim 18 wherein the compound is 2,7-bis(5-piperidinovaleryl)thioxanthene or a pharmaceutically acceptable acid addition salt thereof.

31. The method of claim 18 wherein the compound is 2,7-bis[5-(diethylamino)valeryl]thioxanthene or a pharmaceutically acceptable acid addition salt thereof.

32. The method of claim 18 wherein the compound is 2,7-bis[5-(diallylamino)valeryl]thioxanthene or a pharmaceutically acceptable acid addition salt thereof.

* * * * *

UNITED STATES PATENT AND TRADEMARK OFFICE
CERTIFICATE OF CORRECTION

Page 1 of 2

PATENT NO. : 3,957,988
DATED : May 18, 1976
INVENTOR(S) : Robert W. Fleming and Arthur D. Sill It is certified that error appears in the above-identified patent and that said Letters Patent are hereby corrected as shown below:

*Column 4, lines 42-44, "-NO" should read "-NO".

Column 5, line 50, "The compounds of the invention" should read "The compounds of the present invention". Column 8, lines 56-57, "combine on equivalent" should read "combine one equivalent". Column 16, line 56, "cooled to +20°C." should read "cooled to -20°C."; line 59, "+10°C." should read "-10°C.". Column 19, delete lines 1-37. Column 20, line 53, insert "some of the headings are explained as follows: The "Challenge", that is, inoculation with a virus used is generally fatal to all the untreated, that is, control, animals in the experiment. "Time of death" refers to the average time of death for the untreated animals. The "Treatment" was prophylactic or therapeutic or both. The term "volume" refers to the volume of composition administered per dose which contained the active ingredient dissolved in sterile water which also contained 0.15 percent of hydroxyethylcellulose. The control animals received a sham dosage of the same volume of the vehicle which did not contain the active ingredient. The abbreviation "STR" is survival time ratio, which is calculated by dividing the mean day of death of the control animals into the mean day of death of the treated animals during the period of observation. The activity of the compound in the example involved is further characterized, for example, low, medium, high, and the like. A survival time ratio (STR) of less than 0.90 indicates that the compound was toxic; a ratio of 0.90 to 1.09 indicates that there is no activity; a ratio of 1.10 to 1.19 indicates low or weak activity; a ratio of 1.20 to 1.29 indicates medium activity; and a ratio of 1.30 and greater indicates high activity.

*Applys exclusively to the grant.

UNITED STATES PATENT AND TRADEMARK OFFICE
CERTIFICATE OF CORRECTION

PATENT NO. : 3,957,988
DATED : May 18, 1976
INVENTOR(S) : Robert W. Fleming and Arthur D. Sill It is certified that error appears in the above-identified patent and that said Letters Patent are hereby corrected as shown below:

Table I

| Example No. | Active Ingredient |
|---|---|
| 31 | 2,7-bis(4-piperidinobutyryl)thioxanthene dihydrochloride monohydrate. |
| 32 | 2,7-bis[5-(diethylamino)valeryl]thioxanthene dihydrochloride. |
| 33 & 34 | 2,7-bis(5-piperidinovaleryl)thioxanthene. |
| 35 | 2,7-bis[5-(dimethylamino)valeryl]thioxanthene dihydrochloride. |
| 36 | 2,7-bis[4-(diethylamino)butyryl]thioxanthene dihydrochloride. |
| 37 | 2,7-bis[2-(diethylamino)acetyl]thioxanthene dihydrochloride hydrate. |
| 38 | 2,7-bis(4-morpholinobutyryl)thioxanthene. |

Column 20, line 52, "examples of self-explanatory" should read "examples are self-explanatory". Column 26, claim 27, 1st line, "The method of claim 28" should read "The method of claim 18".

Signed and Sealed this

Eighteenth Day of April 1978

[SEAL]

Attest:

RUTH C. MASON
Attesting Officer

LUTRELLE F. PARKER
Acting Commissioner of Patents and Trademarks